(12) United States Patent
Gustke et al.

(10) Patent No.: US 7,172,554 B2
(45) Date of Patent: Feb. 6, 2007

(54) RETRACTOR INSTRUMENTATION FOR TOTAL HIP ARTHROPLASTY, AND METHODS OF USING SAME

(75) Inventors: Kenneth A. Gustke, Tampa, FL (US); Richard E. Jones, III, Dallas, TX (US); Donald W. Dye, Jr., Pflugerville, TX (US)

(73) Assignee: Zimmer Technology, Inc., Chicago, IL (US)

( * ) Notice: Subject to any disclaimer, the term of this patent is extended or adjusted under 35 U.S.C. 154(b) by 258 days.

(21) Appl. No.: 10/861,549

(22) Filed: Jun. 4, 2004

(65) Prior Publication Data
US 2005/0272980 A1 Dec. 8, 2005

(51) Int. Cl.
*A61B 1/32* (2006.01)
(52) U.S. Cl. .................. 600/213; 600/210; 600/217
(58) Field of Classification Search ........... 600/201, 600/217, 216, 225, 226, 234, 235, 213
See application file for complete search history.

(56) References Cited

U.S. PATENT DOCUMENTS

| | | | | |
|---|---|---|---|---|
| 3,467,079 A | * | 9/1969 | David ................... 600/210 |
| 4,610,243 A | * | 9/1986 | Ray ..................... 600/206 |
| 4,621,619 A | | 11/1986 | Sharpe .................. 128/20 |
| 5,027,793 A | * | 7/1991 | Engelhardt et al. ...... 600/210 |
| 5,303,649 A | * | 4/1994 | Reder et al. ............ 101/363 |
| 5,303,694 A | | 4/1994 | Mikhail ................. 128/20 |
| 5,743,853 A | | 4/1998 | Lauderdale ............ 600/210 |
| 5,954,638 A | | 9/1999 | Spranza, III .......... 600/201 |
| 5,971,920 A | | 10/1999 | Nagel ................... 600/206 |
| 6,010,535 A | | 1/2000 | Shah ..................... 623/22 |
| 6,083,153 A | * | 7/2000 | Rullo et al. ............ 600/217 |
| 6,206,826 B1 | | 3/2001 | Mathews et al. ....... 600/210 |
| 6,267,763 B1 | * | 7/2001 | Castro .................. 606/61 |
| 6,354,994 B1 | * | 3/2002 | Rullo et al. ............ 600/217 |
| 6,547,795 B2 | * | 4/2003 | Schneiderman ......... 606/96 |
| 6,635,062 B2 | * | 10/2003 | Ray et al. ............. 606/96 |
| 6,929,647 B2 | * | 8/2005 | Cohen .................. 606/99 |

\* cited by examiner

*Primary Examiner*—Cary E. O'Connor
(74) *Attorney, Agent, or Firm*—Williams, Morgan & Amerson, P.C.

(57) ABSTRACT

The present invention is directed to retractor instrumentation for total hip arthroplasty, and methods of using same. In one illustrative embodiment, the device comprises a body, a first pin coupled to the body, and a second pin coupled to said body, wherein at least a portion of said first and second pins are adapted to penetrate human bone. In a further illustrative embodiment, a retractor instrumentation set comprises a retractor device, a shaft that is adapted to be removably coupled to the retractor device, and an inserter that is adapted to be removably coupled to the shaft.

58 Claims, 9 Drawing Sheets

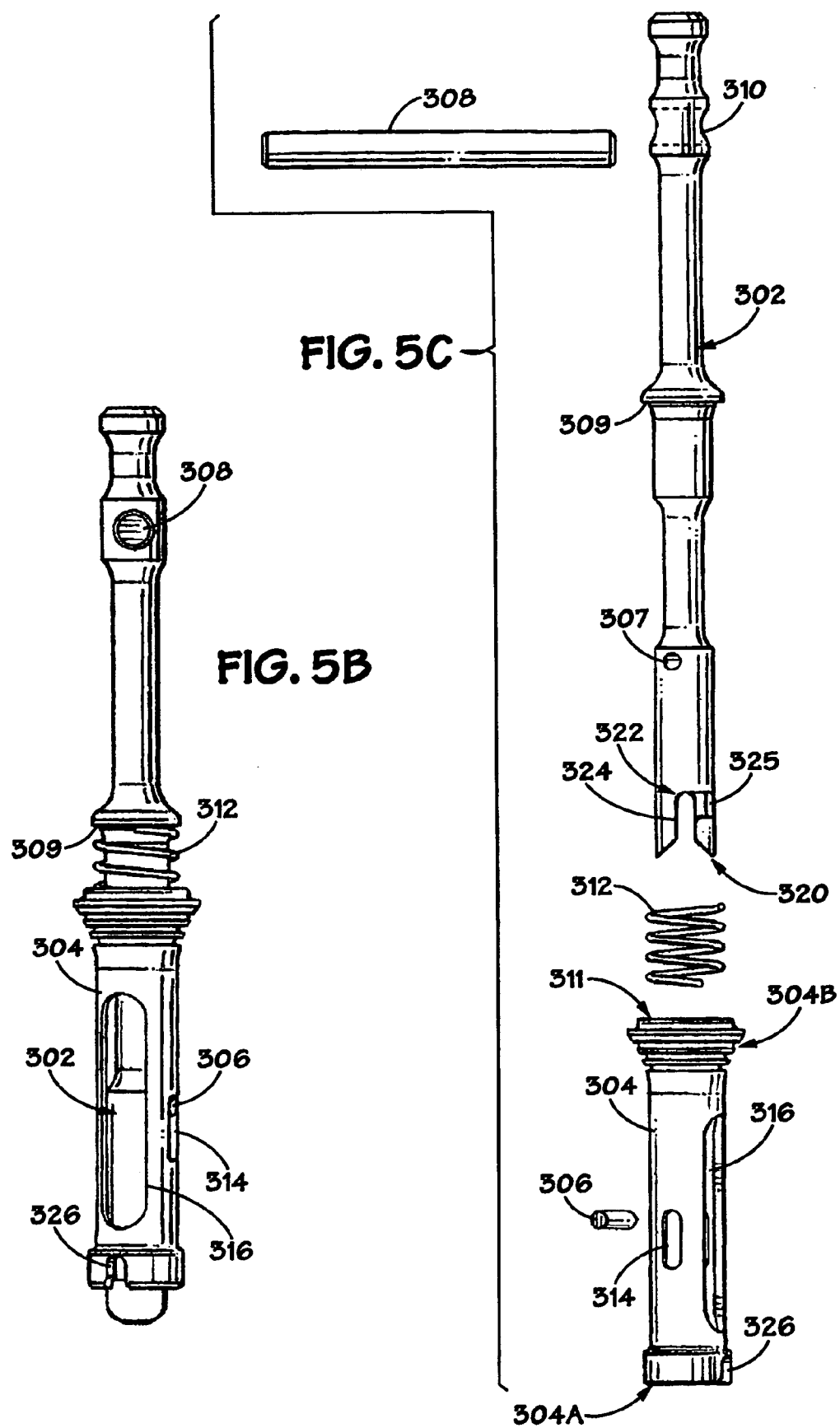

RETRACTOR INSTRUMENTATION FOR TOTAL HIP ARTHROPLASTY, AND METHODS OF USING SAME

BACKGROUND OF THE INVENTION

1. Field of the Invention

The present invention is generally related to the field of orthopedics, and, more particularly, to retractor instrumentation for total hip arthroplasty, and methods of using same.

2. Description of the Related Art

In the field of orthopedics, hip replacement is very common. Each year an estimated 300,000 people undergo hip replacement surgery. That number is expected to increase as the population continues to age, particularly within the United States. Most people have hip replacement surgery because of osteoarthritis, a degenerative joint disease. Basically, hip replacement surgery typically involves positioning a cup, having a plastic liner, in the pelvis, and positioning a stem down inside the femur. A ball on top of the stem is positioned within the cup in a ball-and-socket arrangement thereby allowing the hip to move normally.

Standard hip replacement surgery usually involves a relatively large 10–12" incision, considerable pain, and an extended stay in the hospital, e.g., approximately 7 days. Additional recovery time may be required depending upon the particular patient and the circumstances of the surgeries. In some cases, efforts are being made to perform hip replacement surgery in a less invasive manner. Typically, such less invasive procedures, sometimes referred to as minimally invasive total hip arthroplasty, involve only a 3–4" incision. Such minimally invasive procedures are typically more beneficial to the patient as the patient experiences significantly less pain and regains function of the hip much more quickly. More specifically, minimally invasive surgical techniques involve less cutting through muscles, less blood loss and often shorter hospital stays.

Although such minimally invasive hip replacement surgical techniques are more beneficial to the patient, they tend to be more difficult for a surgeon to perform due to the limited access to the surgical site by virtue of the smaller incision in the patient. When an incision is made in human skin, normally, because of the resilience of the tissue and skin, the incision will tend to remain closed. For a surgeon to perform an operation through the incision, it is necessary that the tissue at the edges of the incision be held back to give the surgeon room and access to perform the operation. Retractors are used for this purpose. In some cases, the retractors are held by assistants and comprise metal instruments having handle portions and hooked ends which can engage the edges of the incision. In other cases, by virtue of the design of the retractor, spaced separating members which engage the incision edges are held in spaced condition by spring or jack means or the like. The latter type of equipment is relatively complicated mechanically, but it may reduce the number of assistants involved as compared to the handheld retractors.

In some cases, prior art retractor methods were beneficial for part of the hip replacement surgery but not for all aspects of the surgery. For example, one illustrative retraction methodology involved use of two upstanding spaced-apart Charnley pins that were traditionally positioned superior to the acetabular and remained in an upright position. Typically, a chain was positioned between the two Charnley pins to assist with the retraction function. During a typical hip replacement procedure, the Charnley pins provided sufficient retraction such that the surgeon could readily access the pelvis area for purposes of installing the replacement acetabular cup. However, when the surgeon then attempted to install the stem in the patient's femur, it was often the case that the upstanding Charnley pins would interfere with part of that procedure. Thus, in some cases, one or more of the Charnley pins were removed, thereby reducing the retraction function of the pins. Moreover, given the tendency towards the minimally invasive hip replacement surgery, with its associated reduced incision length, prior art methodologies of retraction may not be readily adapted or employed in such minimally invasive procedures.

Another problem associated with total hip replacement surgery involves insuring that after the operation is completed the patient's leg is the appropriate length. Historically, problems have arisen with hip replacement surgery wherein the leg length of the patient after surgery is less than ideal, i.e., it is too short or too long relative to its pre-operative length. This may be due to, among other things, the improper positioning of the hip replacement components within the patient. Problems also arose in situations where it was desired to shorten or lengthen a patient's natural leg length during hip replacement surgery. That is, due to a variety of reasons, the surgeon was unable to obtain a desired or target length for the patient's leg after the hip replacement surgery is complete. Fundamentally, problems with achieving correct leg length involved difficulty in identifying and maintaining various reference points that would thereby allow the surgeon to confirm the correct positioning of the patient's leg with the hip replacement components installed in the patient.

The present invention is directed to various devices and methods for solving, or at least reducing the effects of, some or all of the aforementioned problems.

SUMMARY OF THE INVENTION

The present invention is directed to retractor instrumentation for total hip arthroplasty, and methods of using same. In one illustrative embodiment, the device comprises a body, a first pin coupled to the body, and a second pin coupled to said body, wherein at least a portion of said first and second pins are adapted to penetrate human bone.

In another illustrative embodiment, the device comprises a body having a first surface, a first pin coupled to the body, and a second pin coupled to the body, wherein at least a portion of the first and second pins are adapted to penetrate human bone and wherein the first pin has a larger diameter than the second pin and the first pin extends beyond the first surface of the body by a greater distance than the second pin extends beyond the first surface of the body.

In yet another illustrative embodiment, the device comprises a retractor body, a first pin having a pin body, the pin body being coupled to the retractor body, and a second pin coupled to the retractor body, wherein at least a portion of the first and second pins are adapted to penetrate human bone, and wherein the first and second pins are positioned asymmetrically along a first surface of the retractor body.

In a further illustrative embodiment, a retractor instrumentation set comprises a retractor device, a shaft that is adapted to be removably coupled to the retractor device, and an inserter that is adapted to be removably coupled to the shaft. In further embodiments, a reference mark may be formed in the proximal end of the shaft and used for various alignment purposes.

In one illustrative embodiment of the present invention, the method comprises positioning a retractor device adjacent a pelvis of a human patient, the retractor device having first and second pins, inserting the first pin into the patient's pelvis, rotating the retractor device about an axis of the first pin until the retractor device is positioned at a desired location, and inserting the second pin into the patient's pelvis to maintain the retractor at the desired location.

In another illustrative embodiment, the method comprises removably coupling a shaft to a retractor device, the retractor device having first and second pins that are adapted to penetrate bone, and removably coupling an inserter to the shaft.

BRIEF DESCRIPTION OF THE DRAWINGS

The invention may be understood by reference to the following description taken in conjunction with the accompanying drawings, in which like reference numerals identify like elements, and in which:

FIGS. 5A–5C are various views of an illustrative inserter that may be operatively coupled to the shaft depicted in FIGS. 4A–4D;

Figure 1:
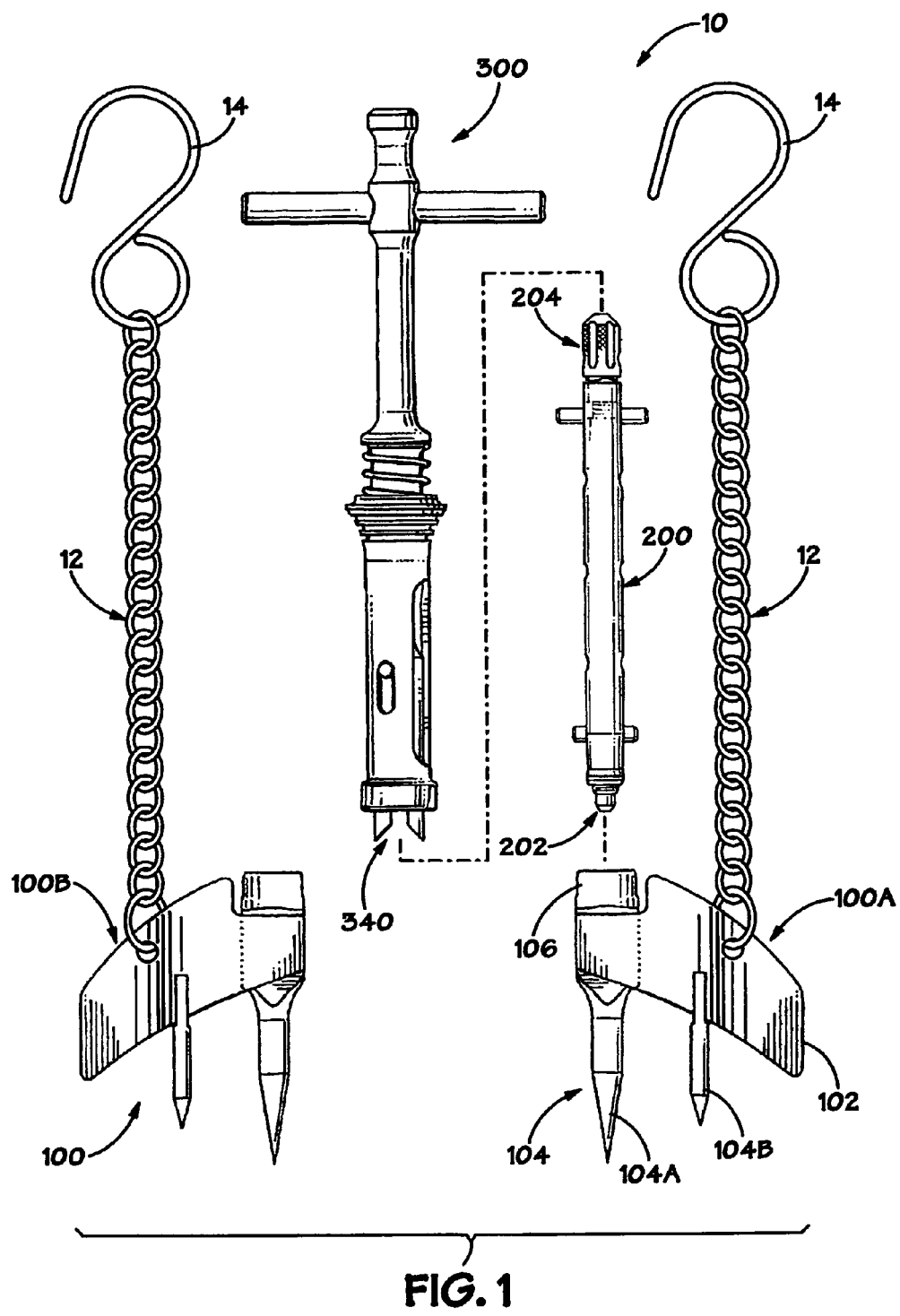
FIG. 1 is a view of one illustrative embodiment of various retractor tools that may be employed in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase. Various anatomical reference terms used herein are intended to have the standard meaning for such terms as understood in the medical community. For example, the application may include reference to the following terms: anterior (the front, as opposed to the posterior); posterior (the back or behind, as opposed to the anterior); inferior (below, as opposed to superior); superior (above, as opposed to inferior); lateral (toward the left or right side of the body, as opposed to medial); medial (in the middle or inside, as opposed to lateral); proximal (toward the beginning, as opposed to distal); and distal (further from the beginning, as opposed to proximal).

In general, the present invention is directed to retractor instrumentation for total hip arthroplasty, and methods of using same. As will be recognized by those skilled in the art after a complete reading of the present application, the present invention may be employed in traditional hip arthroplasty procedures as well as with newer minimally invasive hip arthroplasty procedures. Moreover, the physical configuration of the retractor tool and components of the present invention disclosed herein, as well as the location and placement of the various features of the device, are provided by way of example only Thus, the particular configuration and arrangement of the features of the retractor instrumentation of the present invention, as well as the particular surgical procedures in which it may be employed, should not be considered a limitation of the present invention.

Figure 2:
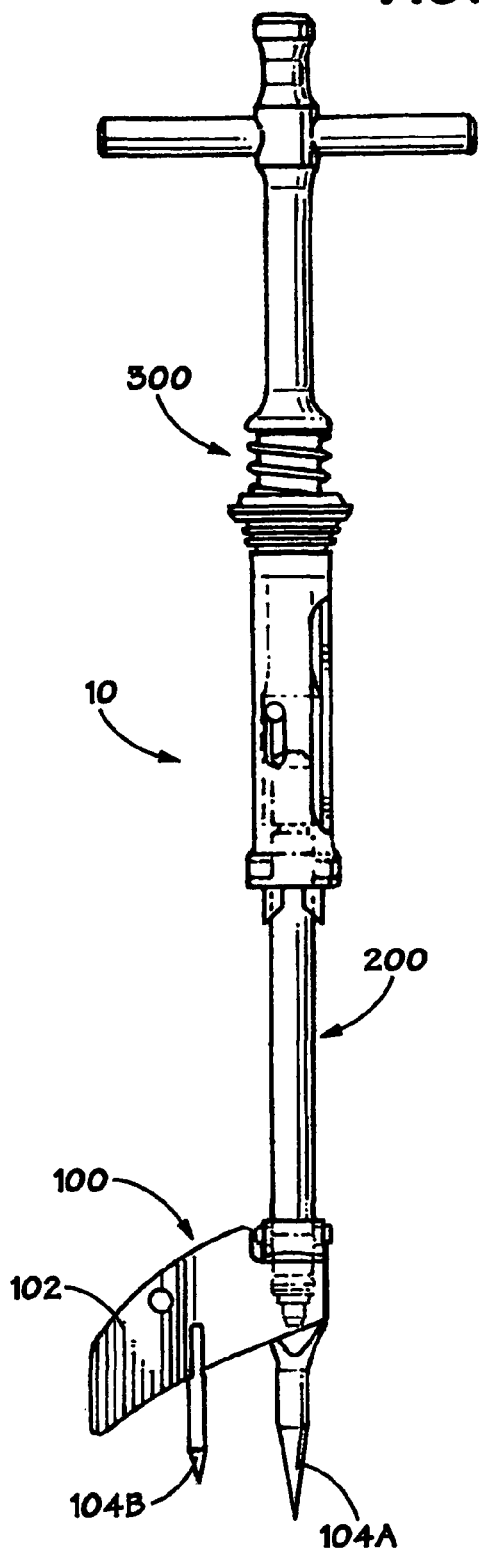
FIG. 2 is a view of some of the retractor components of the present invention in an assembled condition.

FIG. 1 depicts a retractor tool set 10 in accordance with one illustrative embodiment of the present invention. FIG. 2 depicts portions of the retractor tool set 10 in an assembled condition. As indicated in these drawings, the retractor tool set 10 is generally comprised of a plurality of retractor bodies 100, i.e., a right retractor 100A and a left retractor 100B, a shaft 200, and an inserter 300. In general, a distal end 202 of the shaft 200 is adapted to be coupled to the retractor 100A at a collar 106. A proximal end 204 of the shaft 200 is adapted to be coupled to the inserter 300 by insertion of the proximal end 204 of the shaft 200 into the distal end 340 of the inserter 300. The shaft 200 may be used with either of the retractor bodies 100A, 100B depicted in FIG. 1. Additionally, as shown in FIG. 1, the retractors 100A, 100B may have a chain 12 and a hook 14 coupled thereto that may be employed in providing retraction at a surgical site. Each of the retractors 100A, 100B have a plurality of projections, e.g., pins 104, extending from the retractor such that the retractor may be secured to the pelvis of a patient superior to the acetabular region. In the illustrative embodiment depicted herein, each retractor 100A, 100B comprises two pins 104A, 104B for such purposes.

Figure 3C:
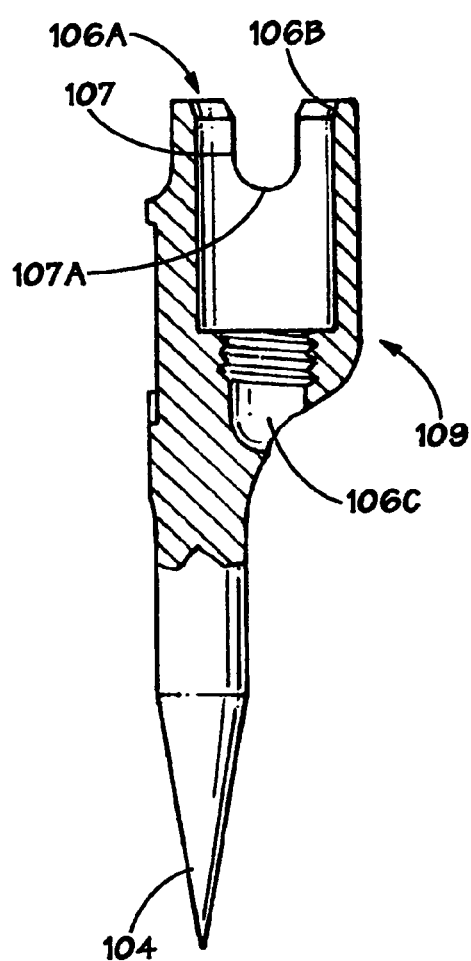
FIGS. 3A–3C are various views of a plurality of retractor bodies in accordance with one embodiment of the present invention.
Figure 3A:
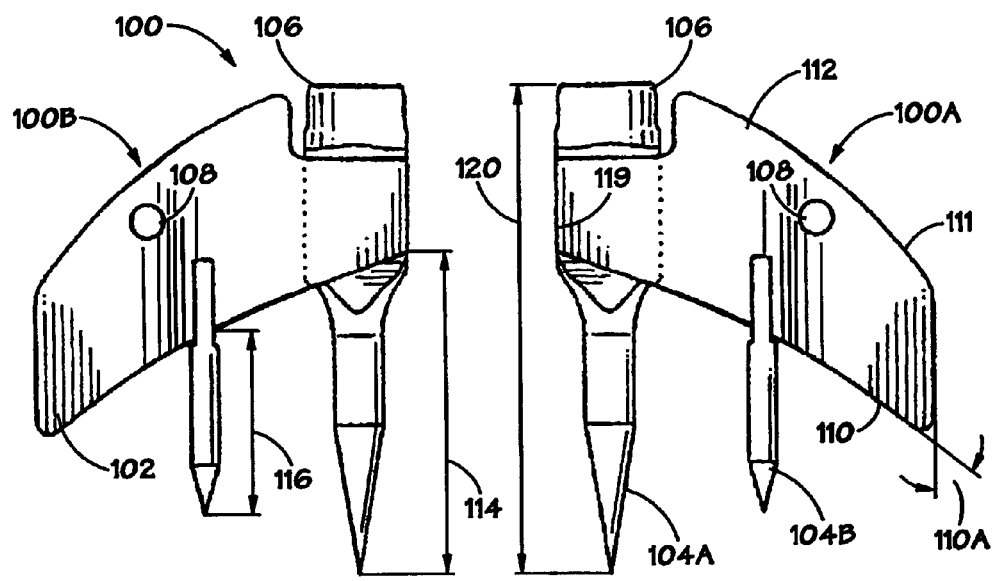
Figure 3B:
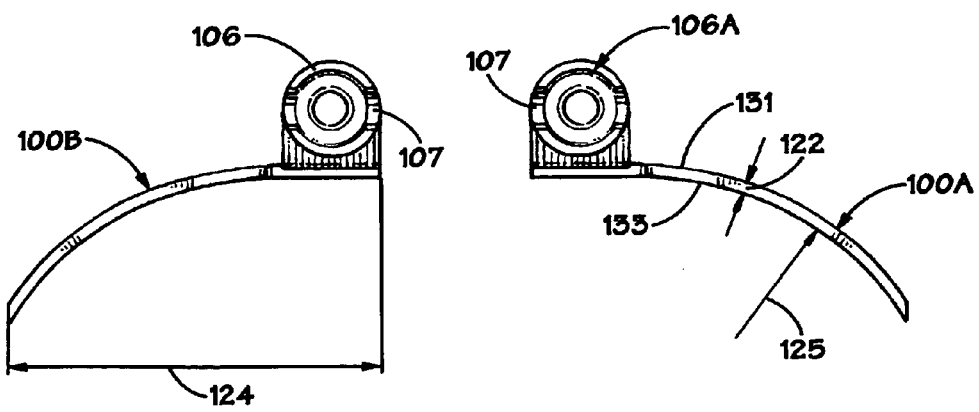

FIGS. 3A–3B are frontal and top views of illustrative retractors 100A, 100B in accordance with one embodiment of the present invention. FIG. 3C is a cross-sectional view of one illustrative embodiment of a pin that may be employed with the present invention. As shown therein, each retractor 100A, 100B is comprised of a body 102, a plurality of pins 104, an opening 108, a first edge 110, and a second edge 111. The collar 106 further comprises a slot 107 for purposes to be described later in the application. In the depicted embodiment, each retractor body 100A, 100B is comprised of two pins 104A, 104B that will be used to secure the retractor in the pelvis of the patient. In the depicted embodiment, the pins 104A, 104B are simply welded to the body 102 of the retractor. The size, number, shape and type of the pins 104A, 104B may vary depending upon the particular application. In the illustrative embodiment depicted herein, the pin 104A is longer and has a greater diameter than that of the pin 104B. For example, the pin 104A may have a length 114 of approximately 1.52" and a diameter of approximately 0.225". The pin 104B may have a length 116 of approximately 0.83" and a diameter of approximately 0.125". The opening 108, when employed, may have a diameter of approximately 0.16". In one illustrative embodiment, an illustrative retractor may have an overall length 120 of approximately 2.31" and an overall width 124 of approximately 1.73". The body 102 may also have a thickness 122 of approximately 0.60". In one illustrative embodiment, the centerline spacing between the pins 104A and 104B may be approximately 0.82". The bottom edge 110 of the retractor body 102 may be cut at an angle 100A of approximately 60–80 degrees with respect to the longitudinal axis of the pin 104A. Note that, in the illustrative embodiment depicted herein, the pins 104A, 104B are asymmetrically positioned along the body 102. Even more specifically, in the depicted embodiment, the first pin 104A is positioned proximate an edge 119 of the body 102 and the pin 104B is positioned approximately midway along the length 124 of the body 102.

In some embodiments of the present invention, having one of the pins, e.g., 104A, longer than the other pin, e.g., 104B, may be beneficial when installing the retractor in a patient. For example, the longer pin, e.g., 104A, may be partially inserted into a patient's pelvis and, thereafter, the retractor body 102 may be rotated about the axis of the longer pin until the retractor body 102 is in the desired orientation and location. The shorter pin, e.g., 104B, does not interfere with this rotation due to its shorter length. Once the retractor body 102 is at the desired location, the second pin 104B may be inserted into the pelvis at the same time the longer pin 104A is driven deeper into the patient's pelvis. Additionally, in some embodiments of the present invention, the pins 104 are asymmetrically positioned on the retractor body. This also facilitates installation in some cases by allowing the retractor body to pivot around one pin that may be located adjacent an edge region of the retractor body. Lastly, one pin may have a greater diameter than the other pin if it is anticipated that the larger diameter pin will experience greater mechanical loads during the installation process.

For ease of explanation, the retractor body 102 has various surfaces that will be referenced with respect to their location when a retractor is installed in a patient's pelvis. That is, as indicated in FIG. 3B, the retractor 100A may have a superior surface 131 and an inferior surface 133. In one illustrative embodiment, at least a portion of the inferior surface 133 may, in one illustrative embodiment, have a radius 125 of approximately 1.44". When the retractor is installed in a patient, the inferior surface 133 will be closer to the acetabular than is the superior surface 131 of the retractor. In the illustrative embodiment depicted herein, the pin 104 comprises an enlarged body 109 (see FIG. 3C) that is adapted to be welded to the superior surface 131 of the retractor body 102. By attaching the body 109 of the pin 104 to the superior surface 131, there is less obstruction of the operating area as compared to the situation if the pin body 109 were welded to the surface 133 of the retractor body 102. Moreover, the body 109 is provided with the opening 106A that is adapted to receive the shaft 200.

Figure 4A:
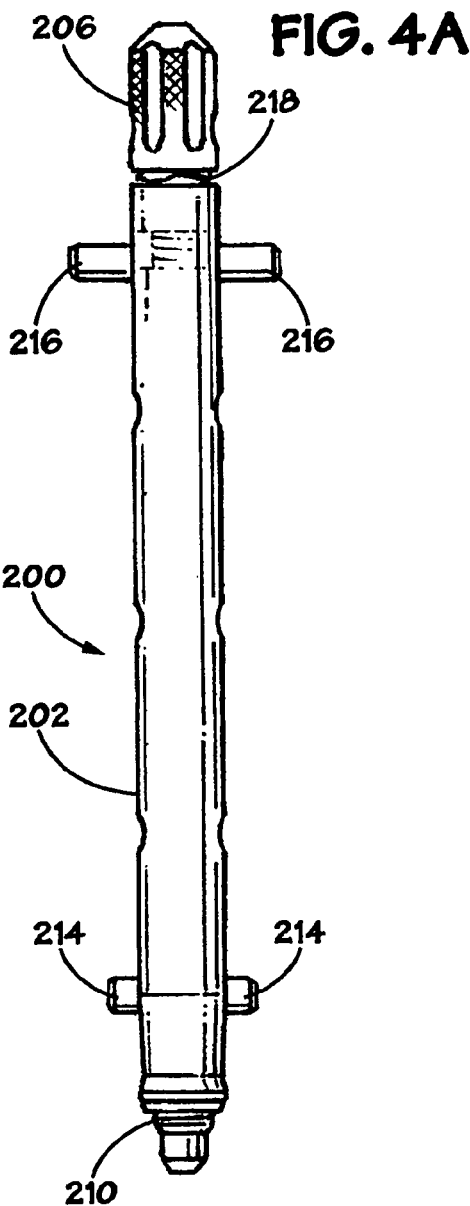
FIGS. 4A–4D are various views of a shaft that may be coupled to the structures depicted in FIGS. 3A–3C.
Figure 4B:
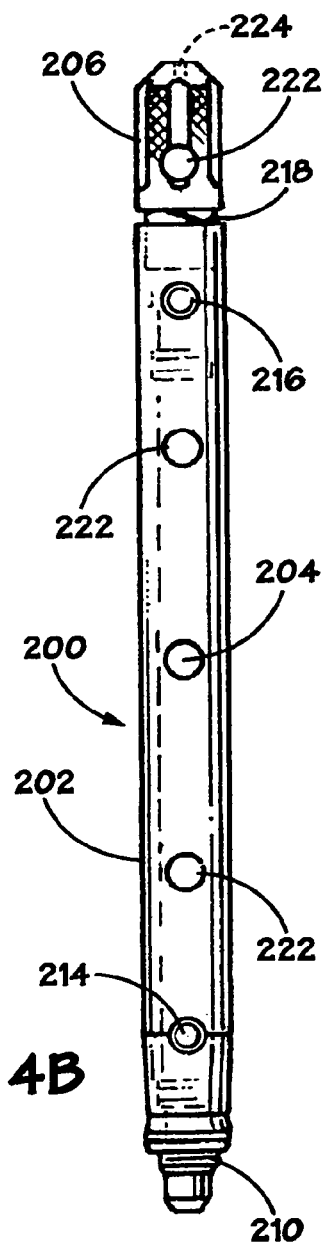
Figure 4D:
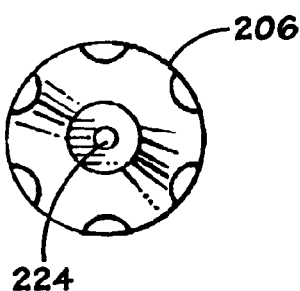
Figure 4C:
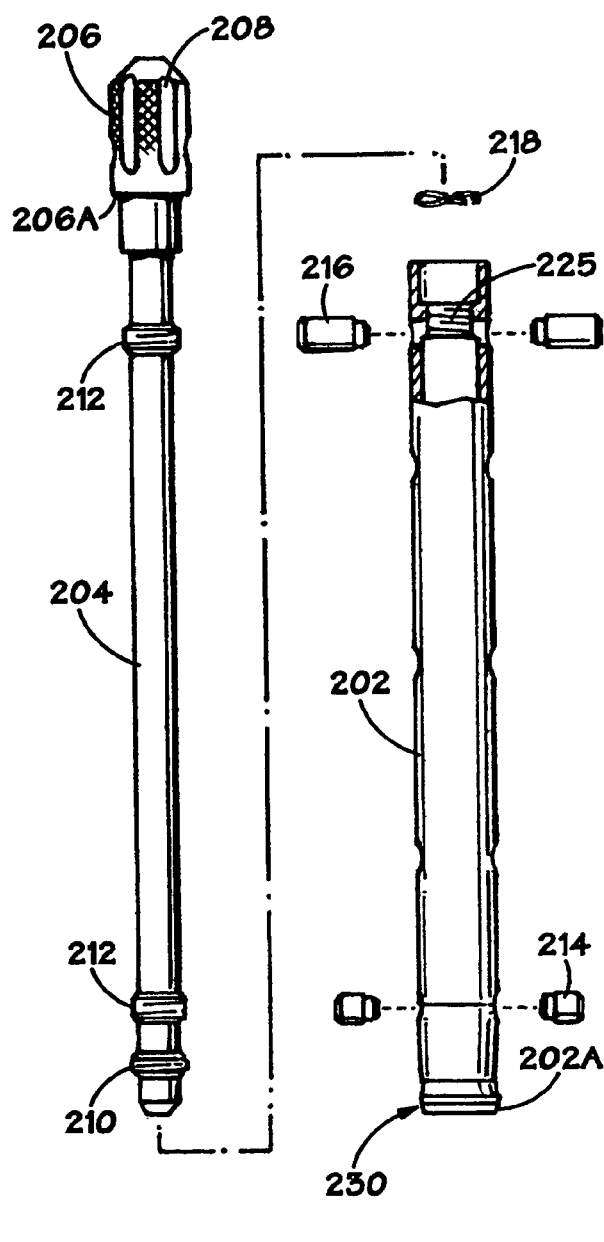

FIGS. 4A–4D depict one illustrative embodiment of the shaft 200 that may be employed in connection with the present invention. As shown therein, the shaft 200 is generally comprised of a tube 202 that is adapted to be positioned over a threaded bar 204. A knurled knob 206 having grooves 208 formed therein is provided on the proximal end of the shaft 200. The threaded bar 204 further comprises a plurality of externally threaded spacers 212 and a threaded end 210. The tube 202 has an internally threaded section 225 within the tube 202. As the tube 202 is positioned over the bar 204, the threaded end 210 and the threaded spacers 212 are threaded past this internally threaded section 225 of the tube 202. After the threaded bar 204 is positioned within the tube 202, a plurality of pins 214, 216 are positioned in openings formed in the tube 202 and welded to the tube 202. The pins 216 are longer than the pins 214 for reasons to be described later in the application. The tube 202 further contains a plurality of openings 222 formed in the side of the tube 202. The openings 222 provide drainage for purposes of cleaning the device. The threaded end 210 of the shaft 200 is adapted to be threadingly coupled to the threaded opening 106C (see FIG. 3C) on one of the retractors 100A, 100B. A spring 218 is provided between the proximal end of the tube 202 and a shoulder 206A of the knurled knob 206. As shown in FIG. 4D, the knurled knob 206 is provided with a reference mark 224 for purposes to be described later in the application. In one particular embodiment, the reference mark 224 is a 1 mm diameter opening or indentation formed in the knurled knob 206. Of course, the reference mark 224 could be any shape or configuration. In one illustrative embodiment, the threaded end 210 of the threaded bar 204 has a ¼-20UNC-2A thread formed thereon to enable quick coupling to one of the retractors 100A, 100B. Typically, the threaded end 210 may have one complete thread formed thereon.

The end 230 of the tube 202 has a tapered edge 202A of approximately 15 degrees. This allows the end 230 of the tube 202 to be readily positioned within the opening 106A (see FIG. 3C) of the collar 106 even when there is a relatively large amount of misalignment between the longitudinal axis of the collar 106 and the longitudinal axis of the tube 202. Moreover, the tapered end 202A of the tube 202 is adapted to seat on the internal tapered surface 106B of the collar 106. In this configuration, the pins 214 on the tube 202 are positioned within the slots 107 on the collar 106, but the pins 214 do not engage the bottom 107A of the slots 107. This configuration allows an insertion force, e.g., a hammer strike, to be transferred through the tube 202 to the pin 104 via the interface between the surface 202A on the tube 202 and the surface 106B in the collar 106. A threaded opening 106C is also provided in the pin body 109. The threaded opening 106C is adapted to be threadingly engaged with the threaded end 210 of the bar 204.

Figure 5A:
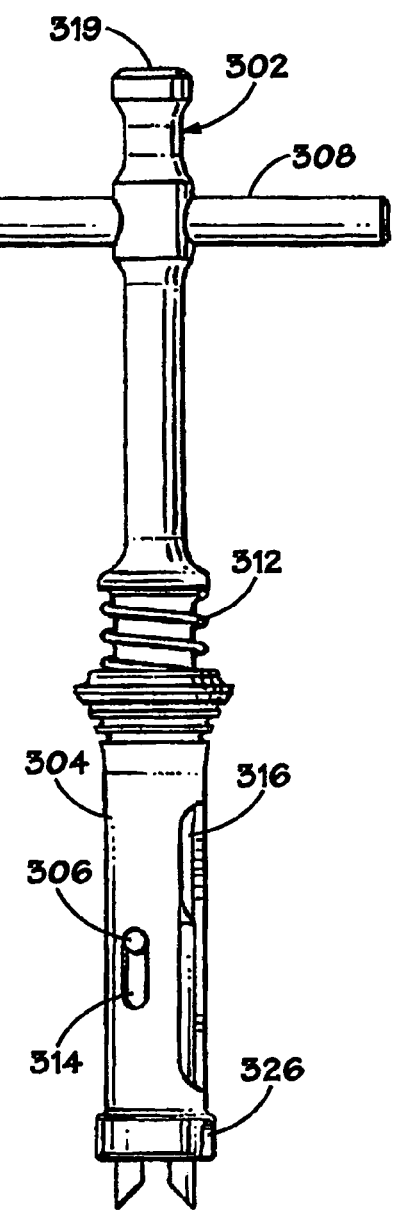

FIGS. 5A–5C depict one illustrative embodiment of the inserter 300 that may be employed with the present invention. As shown therein, the inserter 300 is comprised of a shaft 302, a sleeve 304, a sleeve retaining pin 306, a handle 308 and a spring 312. The shaft 302 has an opening 310 formed therein in which the handle 308 may be positioned there-through and secured to the shaft 302 by welding. The shaft 302 further comprises a J-groove 322 comprised of an axial slot 324 and a radial slot 325. The sleeve 304 further comprises a plurality of slots 314 in the central region of the sleeve 304 and a plurality of slots 326 formed on the distal end 304A of the sleeve 304. The sleeve retaining pin 306 is adapted to be positioned through one of the slots 314 and into an opening 307 formed in the shaft 302. Assembly of the inserter depicted in FIGS. 5A–5C may be accomplished as follows. After the handle 308 is welded to the shaft 302, the spring 312 may be positioned over the shaft 302 such that it engages a shoulder 309 formed on the shaft 302. The sleeve 304 may then be positioned over the distal end of the shaft 302 until a recess 311 formed in the proximal end 304B of the sleeve 304 engages the spring 312. Thereafter, the spring 312 is compressed and the sleeve retaining pin 306 is inserted through one of the slots 314 and into the opening 307 in the shaft 302. At that point, the sleeve 304 is secured to the shaft 302 and the inserter 300 is ready to be coupled to the shaft 200.

Assembly of the retractor 100, the shaft 200 and the inserter 300 may be accomplished as follows. Initially, the shaft 200 is threadingly coupled to the retractor 100. The shaft 200 is asymmetrically positioned on the retractor, i.e., it is coupled to the retractor 100A at a position other than the approximate mid-point of the body 102. In the depicted embodiment, the shaft 200 is asymmetrically coupled to the retractor proximate the edge 119 of the body 102. In the depicted embodiment, this is accomplished by threadingly engaging the threaded end 210 of the shaft 200 with the threaded opening 106C (see FIG. 3C). The threaded connection may be established by rotating the knurled knob 206. As the threaded connection between the threaded end 210 of the shaft 204 and the threaded opening 106C is made up, the end 202A of the tube 202 engages the tapered surface 106B. This forces the tube 202 toward the knurled knob 206, thereby compressing the spring 218 between the proximal end of the tube 202 and the shoulder 206A on the knurled knob 206. The spring 218 acts, in effect, like a lock washer that is useful in reducing the likelihood that the threaded connection between the shaft 200 and the retractor 100 will loosen.

Figure 6C:
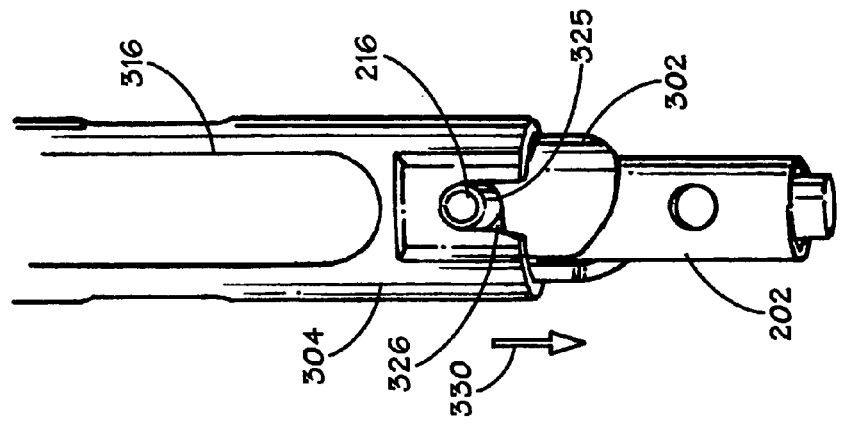
FIGS. 6A–6C disclose an illustrative connection sequence between the shaft and the inserter components of the present invention.
Figure 6B:
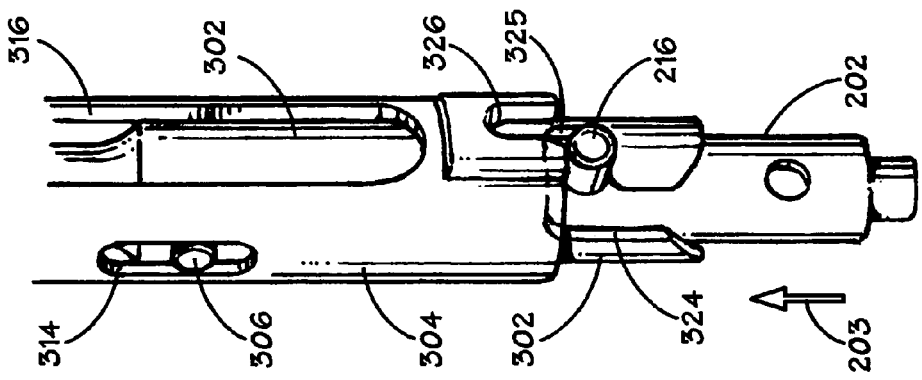
Figure 6A:
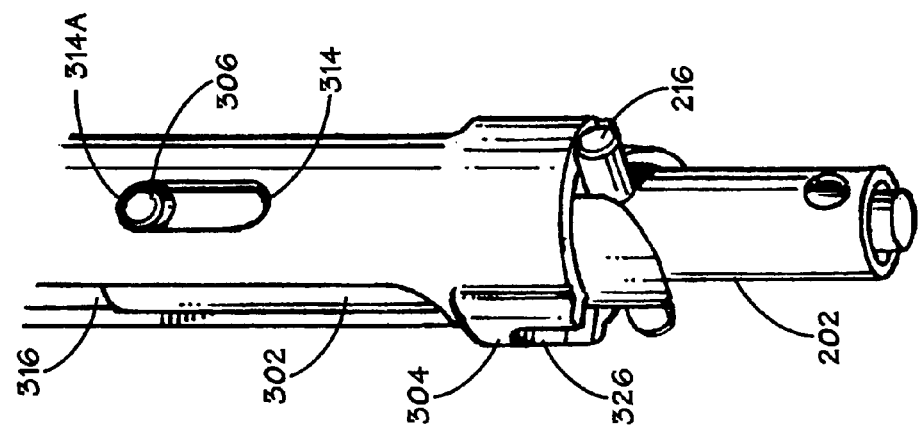

At this point, the combination of the retractor 100 and the shaft 200 may be coupled to the inserter 300. FIGS. 6A–6C depicts an illustrative installation sequence wherein the proximal end 204 of the shaft 200 is positioned within the distal end 340 of the inserter 300. As shown in FIG. 6A, the sleeve 304 is in its fully extended position wherein the sleeve retaining pin 306 engages the proximal end 314A of the slot 314 formed in the sleeve 304. In this position, the spring 312 (not shown in FIG. 6A) is somewhat compressed. The proximal end 204 of the shaft 200 having the pin 216 coupled thereto is positioned proximate the distal end 304A of the sleeve 304. Then, as indicated in FIG. 6B, the shaft 202 is urged in a direction as indicated by the arrow 203 such that the pin 216 travels axially within the axial slot 324 formed in the distal end of the shaft 302. Note that, in this position, the sleeve 304 has moved proximately, as indicated by the movement of the slot 314 relative to the retaining pin 306 as indicated in FIG. 6B. Also note that in FIG. 6B, the pin 216 is partially positioned in the radial slot 325. FIG. 6C depicts the situation where the shaft 202 has been rotated such that the pin 216 is now fully positioned in the radial slot 325 formed on the distal end of the shaft 302. At that time, due to the biasing force applied by the spring 312, the sleeve 304 moves axially in a direction indicated by the arrow 330 until such time as the pin 216 is fully retained within the slot 326 formed in the sleeve 304. In the position depicted in FIG. 6C, the shaft 200 is now securely fixed to the inserter 300. The inserter 300 may be decoupled from the shaft 200 by pulling the sleeve 304 proximally to thereby disengage the pins 216 with the slots 326. Thereafter, the shaft 200 may be rotated and removed from the J-groove formed in the end of the shaft 302.

Figure 7:
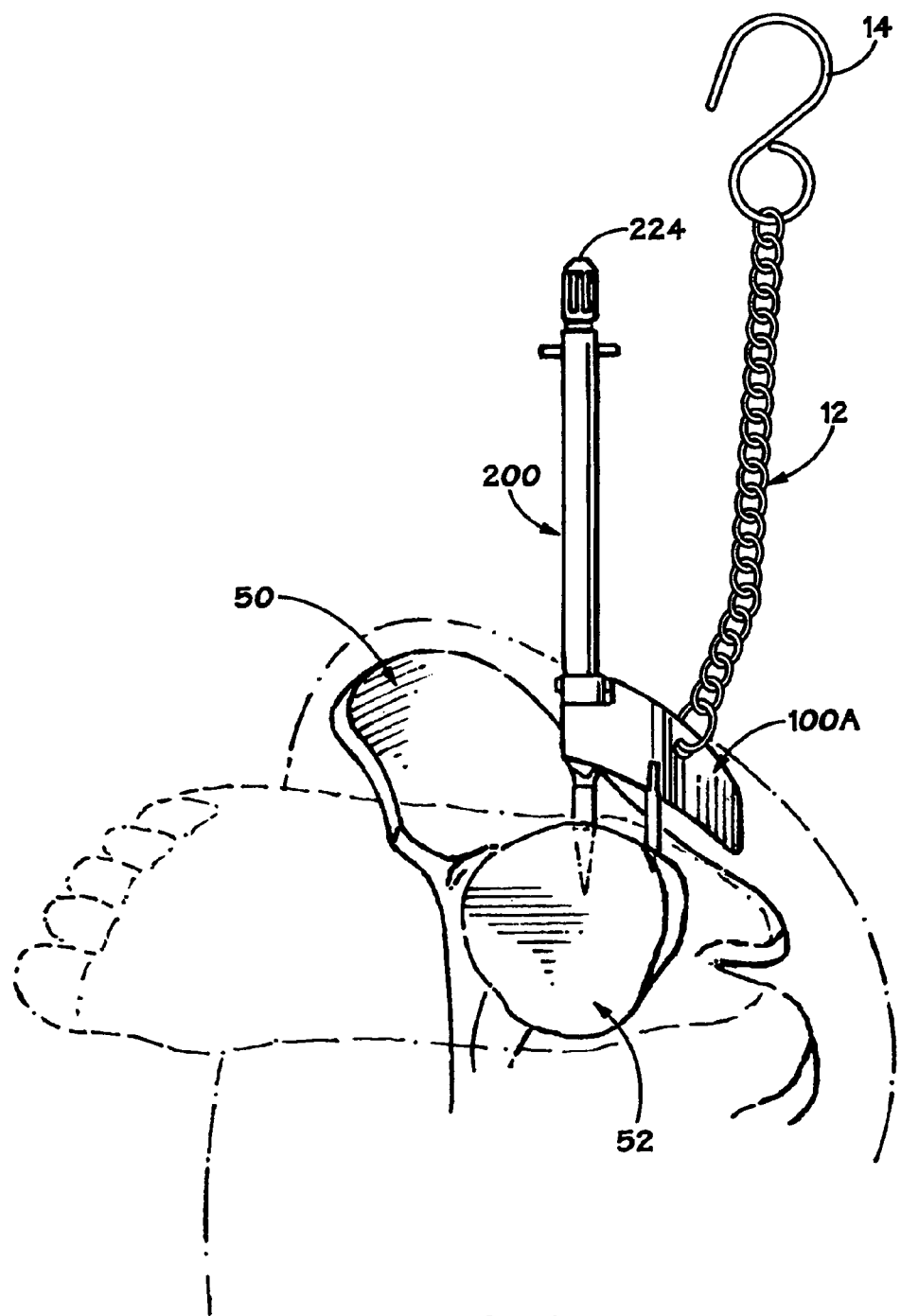
FIG. 7 is a view of some of the retractor components of the present invention positioned in an illustrative pelvis.
Figure 8:
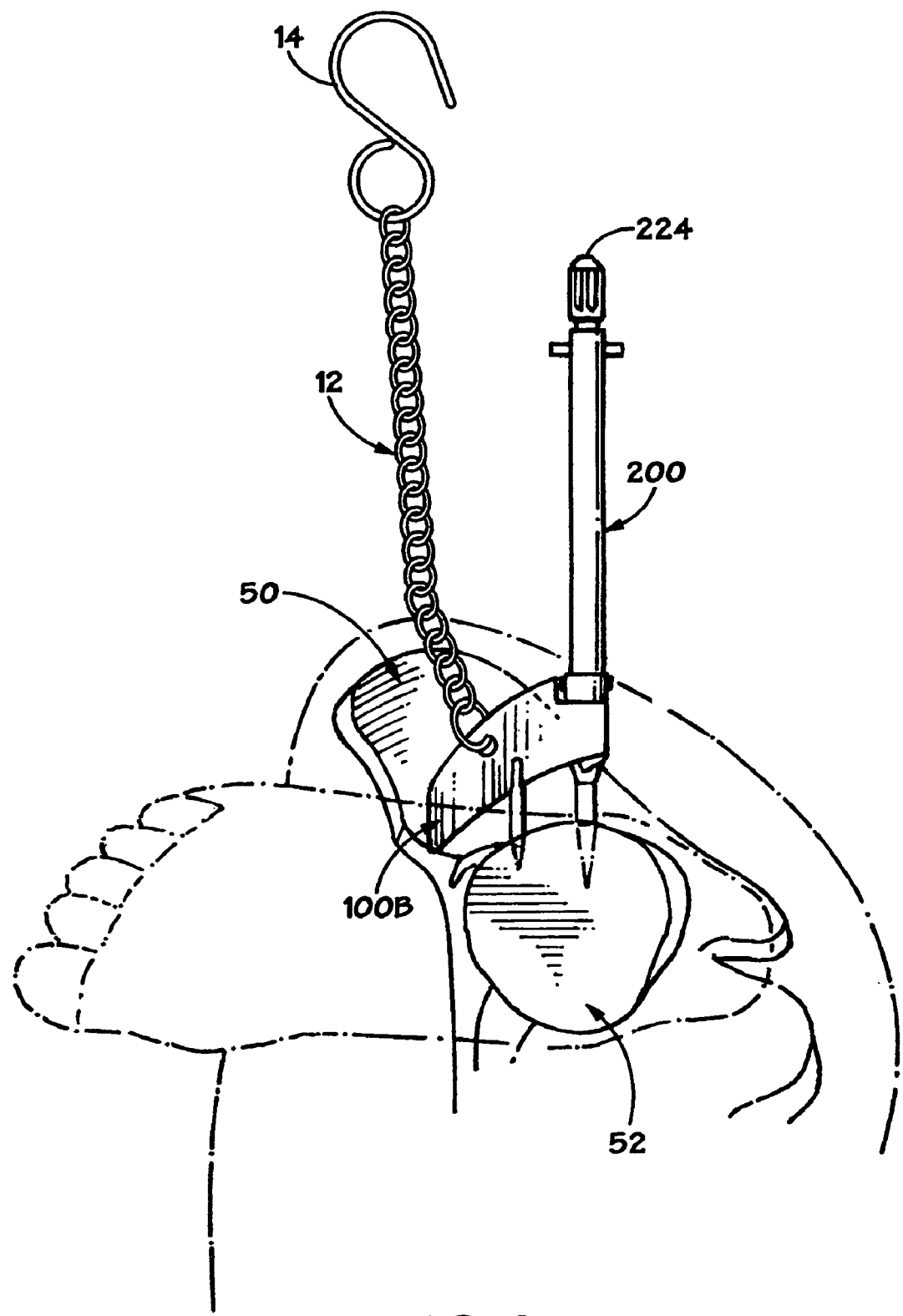
FIG. 8 is another view of some of the components of the present invention positioned in an illustrative pelvis.

The retractors of the present invention may be oriented either posteriorly or anteriorly in the pelvis of a patient. FIG. 7 provides an illustrative example of one of the retractors 100A of the present invention installed posteriorly on a pelvis region 50 of a patient. FIG. 7 is an end view of an illustrative retractor 100A that is installed superior to the acetabulum of a patient above the left leg 52 depicted in FIG. 7. As indicated in FIG. 7, the inserter 300 has been decoupled from the shaft 200. The present invention may be employed where the shaft 200 remains approximately vertical when the patient is positioned on the operating table. If desired, the shaft 200 may be removed from the retractor 100A at any time. The inserter 300 may also be left in place if desired. FIG. 8 depicts the illustrative situation where the retractor 100B is oriented anteriorly on the pelvis region 50. The decision to position the retractor anteriorly or posteriorly may vary depending upon the particular application and surgical methods employed. If the capsule is opened such that the flaps of the incision do not need retraction, the posterior orientation, as shown in FIG. 7, may be employed. If the capsule is opened in a V-shaped incision, the point of the superior flap can be folded superiorly and the small pin 104B of the wing retractor can be driven through this flap, thus holding it out of the way for the rest of the procedure.

As described previously, the reference mark 224 on top of the knurled knob 206 may be used by the surgeon in connection with establishing various reference points for purposes of determining the correct length of the patient's leg before and/or after the surgery has been performed. Typically, a surgeon will drill a reference hole in the patient's femur and use a projection extending therefrom, i.e., a drill bit, as a point of reference for determining correct leg length. The reference mark 224 on top of the knurled knob 206 may be used as a separate reference point on the pelvis. The distance between two such reference points may be used by the surgeon to ascertain the proper leg length of the patient before, during and/or after the surgical procedure, e.g., when the replacement components are being installed in the patient. Since the position of the shaft 200 is fixed relative to the pelvis, the reference mark 224 provides a readily accessible, reliable reference point for establishing the correct leg length of the patient relative to another fixed reference point established on the patient's femur.

An illustrative example of the use of the present invention will now be described. Initially, the doctor may make an incision above the acetabular region of the patient. During this process, an assistant may assemble one of the retractors 100A, the shaft 200 and the inserter 300 in the configuration depicted in FIG. 2. Thereafter, the surgeon may position the retractor 100A superior to the acetabular of the patient and initially push in the pin 104A to a given depth into the pelvis of the patient. With the first pin 104A initially installed at least partially in the pelvis, the surgeon may then position the retractor 100A at any desired orientation by rotating the retractor body 102 about the axis of the pin 104A. Once properly positioned, the surgeon may insert the second pin 104B into the pelvis. This may be done by manually pushing on the retractor 100A or by virtue of one or more hammer strikes applied to the end 319 of the inserter 300. The pins 104A, 104B may be driven to any desired depth within the pelvis such that the retractor 100A is thereby secured to the pelvis and can perform the various functions described herein. Thereafter, the inserter 300 may be de-coupled from the shaft 200. The shaft 200 may then remain in place in the retractor 100A to assist with retraction functions and/or to provide a reference mark for purposes of obtaining the proper leg length of the patient.

As thus described, the present disclosure is directed to various novel retraction instruments, and various methods of using such retractor instrumentation. For example, the present invention is directed to a novel retractor having a body and first and second pins that are coupled to the retractor body. The pins are adapted to penetrate human bone. In another broad aspect, the present invention is directed to a novel three-piece retraction instrumentation assembly. In the disclosed embodiment, the assembly is comprised of a retractor, a shaft adapted to be removably coupled to the retractor, and an inserter that is adapted to be removably coupled to the shaft. In yet another aspect, in the illustrative embodiment depicted herein, the attachment of the shaft to the retractor body is asymmetrical in nature. That is, in the embodiment described herein, the shaft 200 is adapted to be coupled to the retractor 100 adjacent one edge 119 of the retractor body 102. The interface between the beveled surface 202A and the surface 106B is also novel as it allows the shaft 200 and the retractor 100 to be coupled to one another even if there is an initial misalignment between the components. Various other novel and useful aspects of the present invention will be recognized by those skilled in the art after a complete reading of the present application.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A retractor device, comprising:
    a body;
    a first pin permanently attached to and extending from said body; and
    a second pin permanently attached to and extending from said body, wherein at least a portion of said first and second pins are adapted to penetrate human bone, and wherein said first and second pins are positioned asymmetrically along a first surface of said body.

2. The retractor of claim 1, wherein said first and second pins have different diameters.

3. The retractor of claim 1, wherein said first pin has a larger diameter than said second pin and said first pin extends beyond a first surface of said body by a greater distance than said second pin extends beyond said first surface of said body.

4. The retractor of claim 3, wherein said first surface of said body is positioned at an angle relative to a longitudinal centerline of said first pin.

5. The retractor of claim 4, wherein said angle ranges from approximately 60–80 degrees.

6. The retractor of claim 1, wherein said first and second pins have differing lengths.

7. The retractor of claim 1, wherein said first pin is positioned proximate a first edge of said body and said second pin is laterally spaced apart from said first pin.

8. The retractor of claim 1, wherein said first and second pins are laterally spaced apart from one another.

9. The retractor of claim 1, wherein at least a portion of said body has a curved surface that is adapted to be positioned adjacent and superior to an acetabular region of a human patient.

10. The retractor of claim 1, wherein said first pin further comprises a pin body that is permanently attached to said body.

11. The retractor of claim 1, further comprising a shaft that is removably coupled to said retractor device.

12. The retractor of claim 11, wherein said shaft is removably coupled to said retractor device by a threaded connection.

13. The retractor of claim 11, wherein said shaft further comprises a reference mark formed in a proximal end of said shaft.

14. The retractor of claim 11, further comprising an inserter that is adapted to be removably coupled to a proximate end of said shaft.

15. The retractor of claim 14, wherein said inserter comprises a handle and a proximal end surface, said proximal end surface adapted to receive a hammer strike.

16. The retractor of claim 14, wherein said inserter comprises a movable outer sleeve positioned around a rod, a distal end of said movable outer sleeve having a groove formed therein that is adapted to engage a pin coupled to a proximal end of said shaft.

17. A retractor device, comprising:
    a body having a first surface;
    a first pin permanently attached to and extending from said body; and
    a second pin permanently attached to and extending from said body, wherein at least a portion of said first and second pins are adapted to penetrate human bone and wherein said first pin has a larger diameter than said second pin and said first pin extends beyond said first surface of said body by a greater distance than said second pin extends beyond said first surface of said body, and wherein said first and second pins are positioned asymmetrically along a first surface of said body.

18. The retractor of claim 17, wherein said first pin is positioned proximate a first edge of said body and said second pin is laterally spaced apart from said first pin.

19. The retractor of claim 17, wherein at least a portion of said body has a curved surface that is adapted to be positioned adjacent and superior to an acetabular region of a human patient.

20. The retractor of claim 17, wherein said first pin further comprises a pin body that is welded to said body.

21. The retractor of claim 17, further comprising a shaft that is removably coupled to said retractor device.

22. The retractor of claim 21, wherein said shaft is removably coupled to said retractor device by a threaded connection.

23. The retractor of claim 21, wherein said shaft further comprises a reference mark formed in a proximal end of said shaft.

24. The retractor of claim 21, further comprising an inserter that is adapted to be removably coupled to a proximate end of said shaft.

25. The retractor of claim 24, wherein said inserter comprises a handle and a proximal end surface, said proximal end surface adapted to receive a hammer strike.

26. The retractor of claim 24, wherein said insert comprises a movable outer sleeve positioned around a rod, a distal end of said movable outer sleeve having a groove formed therein that is adapted to engage a pin coupled to a proximal end of said shaft.

27. A retractor instrumentation set, comprising:
a retractor device comprising a body and first and second pins permanently attached to and extending from said body, said first and second pins being adapted to penetrate human bone;
a shaft that is adapted to be removably coupled to said retractor device; and
an inserter that is adapted to be removably coupled to said shaft.

28. The retractor instrumentation set of claim 27, wherein said first and second pins have different diameters.

29. The retractor instrumentation set of claim 27, wherein said first and second pins have differing lengths.

30. The retractor instrumentation set of claim 27, wherein said first pin has a larger diameter than said second pin and said first pin extends beyond said first surface of said body by a greater distance than said second pin extends beyond said first surface of said body.

31. The retractor instrument set of claim 27, wherein said first and second pins are positioned asymmetrically along a first surface of said body.

32. The retractor instrumentation set of claim 27, wherein said body has a curved surface that is adapted to be positioned adjacent and superior to an acetabular region of a human patient.

33. The retractor instrumentation set of claim 27, wherein said shaft is removably coupled to said retractor device by a threaded connection.

34. The retractor instrumentation set of claim 27, wherein said shaft further comprises a reference mark formed in a proximal end of said shaft.

35. The retractor instrumentation set of claim 27, wherein said inserter comprises a handle and a proximal end surface, said proximal end surface adapted to receive a hammer strike.

36. The retractor instrumentation set of claim 27, wherein said insert comprises a movable outer sleeve positioned around a rod, a distal end of said movable outer sleeve having a groove formed therein that is adapted to engage a pin coupled to a proximal end of said shaft.

37. The retractor instrumentation set of claim 27, wherein said retractor device has an opening and wherein a portion of said shaft is adapted to be positioned in said opening, said shaft comprising a beveled surface that is adapted to engage a surface within said opening.

38. A method, comprising:
positioning a retractor device adjacent a pelvis of a human patient, said retractor device having first and second pins permanently attached to and extending from said body, said first and second pins being adapted to penetrate human bone;
inserting said first pin into said patient's pelvis;
rotating said retractor device about an axis of said first pin until said retractor device is positioned at a desired location; and
inserting said second pin into said patient's pelvis to maintain said retractor at said desired location.

39. The method of claim 38, wherein said first and second pins have differing diameters.

40. The method of claim 38, wherein said first pin has a larger diameter than said second pin and said first pin extends beyond a first surface of said retractor device by a greater distance than said second pin extends beyond said first surface of said retractor device.

41. The method of claim 38, wherein said first and second pins have differing lengths.

42. The method of claim 38, wherein said first and second pins are positioned asymmetrically along a first surface of said device.

43. The method of claim 38, wherein inserting said first pin into said patient's pelvis is performed by striking an end of an inserter that is operatively coupled to said retractor device.

44. The method of claim 38, wherein inserting said second pin into said patient's pelvis to maintain said retractor at said desired location is performed by striking an end of an inserter that is operatively coupled to said retractor device.

45. The method of claim 38, further comprising, prior to positioning said retractor device adjacent said pelvis, removably coupling a shaft to said retractor device and removably coupling an inserter to said shaft.

46. The method of claim 45, further comprising, after said second pin is inserted into said pelvis, decoupling said inserter from said retractor device while leaving said shaft coupled to said retractor device.

47. A retractor device, comprising:
a body;
a first pin permanently attached to and extending from said body;
a second pin permanently attached to and extending from said body, wherein at least a portion of said first and second pins are adapted to penetrate human bone; and
a shaft that is removably coupled to said retractor device, wherein said shaft further comprises a reference mark formed in a proximal end of said shaft.

48. The retractor of claim 47, wherein said shaft is removably coupled to said retractor device by a threaded connection.

49. The retractor of claim 47, further comprising an inserter that is adapted to be removably coupled to a proximate end of said shaft.

50. A retractor device, comprising:
a body;
a first pin permanently attached to and extending from said body;
a second pin permanently attached to and extending from said body, wherein at least a portion of said first and second pins are adapted to penetrate human bone;
a shaft that is removably coupled to said retractor device; and
an inserter that is adapted to be removably coupled to a proximate end of said shaft.

51. The retractor of claim 50, wherein said inserter comprises a handle and a proximal end surface, said proximal end surface adapted to receive a hammer strike.

52. The retractor of claim 50, wherein said insert comprises a movable outer sleeve positioned around a rod, a distal end of said movable outer sleeve having a groove formed therein that is adapted to engage a pin coupled to a proximal end of said shaft.

53. A retractor device, comprising:
a body having a first surface;
a first pin permanently attached to and extending from said body;
a second pin permanently attached to and extending from said body, wherein at least a portion of said first and second pins are adapted to penetrate human bone and wherein said first pin has a larger diameter than said second pin and said first pin extends beyond said first surface of said body by a greater distance than said second pin extends beyond said first surface of said body; and a shaft that is removably coupled to said retractor device, wherein said shaft further comprises a reference mark formed in a proximal end of said shaft.

54. The retractor of claim 53, further comprising an inserter that is adapted to be removably coupled to a proximate end of said shaft.

55. The retractor of claim 54, wherein said inserter comprises a handle and a proximal end surface, said proximal end surface adapted to receive a hammer strike.

56. A retractor device, comprising:
a body having a first surface;
a first pin permanently attached to and extending from said body;
a second pin permanently attached to and extending from said body, wherein at least a portion of said first and second pins are adapted to penetrate human bone and wherein said first pin has a larger diameter than said second pin and said first pin extends beyond said first surface of said body by a greater distance than said second pin extends beyond said first surface of said body;
a shaft that is removably coupled to said retractor device; and
an inserter that is adapted to be removably coupled to a proximate end of said shaft.

57. The retractor of claim 56, wherein said inserter comprises a handle and a proximal end surface, said proximal end surface adapted to receive a hammer strike.

58. The retractor of claim 56, wherein said insert comprises a movable outer sleeve positioned around a rod, a distal end of said movable outer sleeve having a groove formed therein that is adapted to engage a pin coupled to a proximal end of said shaft.

* * * * *